United States Patent
Pissanos et al.

[11] Patent Number: 6,128,620
[45] Date of Patent: Oct. 3, 2000

[54] MEDICAL DATABASE FOR LITIGATION

[76] Inventors: Patricia L. Pissanos, 475 Cedar Crest Dr.; Stephen M. Beasley, 2464 Jamestown Dr., both of Hoover, Ala. 35216

[21] Appl. No.: 09/241,386

[22] Filed: Feb. 2, 1999

[51] Int. Cl.[7] .................................................. G06F 17/30
[52] U.S. Cl. .......................... 707/102; 707/104; 707/505; 705/2; 705/3; 345/352
[58] Field of Search .......................... 705/2, 3; 395/768; 707/508, 3, 104, 200, 505, 102; 345/352

[56] References Cited

U.S. PATENT DOCUMENTS

| | | | |
|---|---|---|---|
| 5,546,580 | 8/1996 | Seliger et al. | 705/2 |
| 5,640,501 | 6/1997 | Turpin | 395/768 |
| 5,758,095 | 5/1998 | Albaum et al. | 707/508 |
| 5,812,984 | 9/1998 | Goltra | 705/3 |
| 5,819,229 | 10/1998 | Boppe | 705/2 |
| 5,845,255 | 12/1998 | Mayaud | 705/3 |
| 5,875,431 | 2/1999 | Heckman et al. | 705/7 |
| 5,912,818 | 6/1999 | McGrady et al. | 364/479.02 |
| 5,935,060 | 8/1999 | Lliff | 600/300 |
| 6,014,631 | 1/2000 | Teagarden et al. | 705/3 |
| 6,042,005 | 3/2000 | Basile et al. | 235/382 |
| 6,067,524 | 5/2000 | Byerly et al. | 705/3 |

*Primary Examiner*—Jean R. Homere

[57] ABSTRACT

A medical database and associated methods are especially suited for compiling information in a medical malpractice situation. A general medical database is provided and specific medical information corresponding to a given situation is entered. Entry of the information automatically cross-references some terms of the entered data to definitions in the general medical database. Terms are readily looked up when reviewing specific medical information and definitions are easily inserted where desired. A drug reference display provides two-way lookup from drugs to their side effects (or contraindications or interactions) and back. Significant information from an entered medical chronology is easily copied to a significant information section when a reviewer finds the information important.

9 Claims, 15 Drawing Sheets

☐ JB test case 10/11/98
　📄 Chronology
　📄 Significant Information
　　╬ A. Preexisting Symptoms
　　▭ B. Preexisting Illnesses/Medical History
　　▭ C. Post Alleged Injury Medical History
　　╬ D. Accident or Alleged Injury Description
　　▭ E. Other Accidents/ Injuries
　　╬ F. Behaviors or Comments Suspect for Malingering
　　▭ G. Surgical/ Medical/ Dental Implants or Prosthesis
　　▭ H. Exposure to Asbestos/ Dyes/ Pesticides/ Chemotherapy/ Lead/ Mercury
　　▭ I. Alcohol/ Drug/ Tobacco Usage
　　▭ J. Mental/ Emotional History
　　▭ K. Other Legal Actions/ Worker's Compensation Claims
　　▭ L. Activity Level/ Hobbies and Special Interests
　　▭ M. Mental Cognizance
　　▭ N. Medications
　　▭ O. Drug/ Alcohol [ETOH] Testing
　　▭ P. Allergies

Significant Information Items

B _ Preexisting Illnesses/Medical History

Example Case

Item Date: 5/5/55

Item Body: rising; elevated; incre

Item Source Pg #: 5555

Record:1

Delete

Drug Reference - Side Effects And Contra Indications — 412

Side Effects | Contraindications | Interactions

From Allegra Caps [Hoechst Marion Roussel]

DROWSINESS

Print / All

Drugs

With Side Effect DROWSINESS

Print / All

- Accupril Tabs [Parke-Davis]
- Accutane Caps [Roche Laboratories]
- Acel-Imune [Lederle Labs]
- Aceon Tabs [Rhone-Poulenc Rorer]
- ActHIB [Pasteur Merieux Connaught]
- Actified Allergy Daytime/Nighttime Caplets [Warner-La...
- Actified Cold and Allergy Tabs [Warner-Lambert]
- Actified Cold and Sinus Caplets and Tabs [Warner-La...
- Actified Sinus Daytime/Nighttime Tabs and Caplets [M...
- Adalat CC Tabs [Bayer]
- Adenoscan [Fujisawa]
- Agrylin Caps [Roberts]
- Akineton Injection [Knoll Labs]
- Akineton Tabs [Knoll Labs]
- Albalon Ophthalmic Solution with Liquifilm [Allergan]
- Aldactazide Tabs [Searle]
- Aldactone Tabs [Searle]
- Alfenta Injection [Janssen]
- Alferon N Injection [Interferon]
- Alka-Seltzer Plus Cold and Cough Medicine [Bayer]

Close

MEDICAL DATABASE FOR LITIGATION

COPYRIGHT NOTICE

This patent application includes appendices that are subject to copyright. The owner of the copyright has no objection to simply copying of the copyrighted material as part of copying this application or patent. However, all other rights in the copyrighted material are reserved.

BACKGROUND OF THE INVENTION

The present invention relates to a medical database and a corresponding method. More specifically, it relates to a medical database for litigation (i.e., pending as well as potential lawsuits or claims) and methods of generating and using a medical malpractice database. Such potential and pending litigations (lawsuits and claims) include personal injury, workman's compensation, wrongful death, products liability and medical malpractice cases and any other case where medical records are involved.

Various medical databases have been used for years. Programs allowing families easy access to medical information have been used over the last few years. Often a consumer loads the program on his or her computer and then customizes the files associated with the program by entering, for example, a list of medical drugs that the person is taking. Such programs often can provide an indication if the use of the drugs in combination poses a significant risk of an adverse drug reaction. Often the programs provide information about the drug such as what it is commonly prescribed for, side effects, etc. Although some of the programs are useful for providing consumers medical information, they may lack features that would provide sophisticated analysis necessary for use in other contexts.

Apart from computer programs that provide consumers easy access to medical information it is necessary to compile large amounts of specific medical information (i.e., medical information taken from medical records or medical forms specific to the situation) in connection with defending or prosecuting a lawsuit or potential lawsuit. In order to properly enter such information in a database created or customized for a specific litigation, it is often necessary to use paralegals, medical personnel, or attorneys to perform some of data entry and processing for the litigation. This increases the cost of the process.

OBJECTS AND SUMMARY OF THE INVENTION

Accordingly, it is a primary object of the present invention to provide a new and improved medical database and associated techniques of assembly and use of the database.

A more specific object of the present invention is to provide a medical database with highly sophisticated cross-referencing capability where accessing an entry in one part of the database provides easy access to an entry in another part of the database.

A further object of the present invention is to provide a medical database where information from one part of the database may selectively be easily pasted to another part of the database.

Yet another object of the present invention is to provide a medical database for litigation and associated techniques of assembly and use.

A further object of the present invention is to provide a medical database for litigation where less skilled individuals can enter raw information easily and more skilled individuals can further process the information later.

The above and other features of the present invention which will be more readily understood when the following detailed description is considered in conjunction with the accompanying drawings are realized by a method of generating a medical database for litigation, the steps including: supplying a general medical database; and entering specific medical information taken from medical records, medical forms, or situations such that information is entered using the selected template relative to at least one given medical malpractice litigation in a storage medium. Upon entry of the specific medical information, at least some terms in the specific medical information are automatically referenced to definitions or examples of such terms in the general medical database such that selecting one of the referenced terms in the specific medical information causes the display of a corresponding definition or example in the general medical database. The general medical database and the specific medical information together constitute a customized database. The entering step involves entering specific medical information relative to a plurality of litigations. The entering step allows selection of one of a plurality of templates corresponding to specific medical records forms or situations such that information is entered using the selected template. The general medical database includes a drug reference section and a corresponding drug information section, the drug information selected from the group consisting of: side effects and contraindications. Selecting a particular side effect or contraindication that is displayed causes the display of drugs having the particular side effect or contraindication. Selecting a given drug causes the display of the drug information for the selected drug.

The specific medical information taken from medical records, medical forms, or situations such that information is entered using the selected template includes a medical chronology and, upon selecting a term in the medical chronology, a definition or example of the term from the general medical database is displayed. Actuation of a combined copy-paste command automatically copies and pastes the displayed definition or example or parts thereof to the medical chronology.

Upon reviewing the specific medical information, selection of a portion of the specific medical information copies the selected portion to a significant information portion, the significant information portion representing parts of the specific medical information that a reviewer thinks are most significant. The method further includes printing the specific medical information arranged by date, medical provider, or significant information as selected by a user.

The invention may alternately be described as a customized database made using the method above.

The invention may alternately be described as a database method for a medical database, the steps including: supplying a general medical database, the general medical database including a drug reference section and a corresponding drug information section, the drug information selected from the group consisting of: side effects and contraindications; and selecting a given drug which causes the display of the drug information for the selected drug. Selecting a particular side effect or contraindication that is displayed corresponding to a previously selected drug causes the display of drugs having the particular side effect or contraindication. The method further includes entering specific medical information relative to at least one given litigation in a storage medium. Upon entry of the specific medical information, at least some terms in the specific medical information are automatically referenced to definitions or examples of such terms in the general medical database such that selecting one of the referenced terms in the specific medical information causes the display of a corresponding definition or example in the general medical database. The general medical database and the specific medical information together constitute a customized database. The specific medical information includes a medical chronology and, upon selecting a term in the medical chronology, a definition or example of the term from the general medical database is displayed, and wherein actuation of a combined copy-paste command automatically copies and pastes the displayed definition or example or parts thereof to the medical chronology.

The invention may alternately be described as a method of generating a medical database for litigation, the steps including: supplying a general medical database; and entering specific medical information relative to at least one given medical malpractice litigation in a storage medium. Upon reviewing the specific medical information, selection of a portion of the specific medical information copies the selected portion to a significant information portion, the significant information portion representing parts of the specific medical information that a reviewer thinks are most significant. The general medical database and the specific medical information together constitute a customized database. Upon entry of the specific medical information, at least some terms in the specific medical information are automatically referenced to definitions or examples of such terms in the general medical database such that selecting one of the referenced terms in the specific medical information causes the display of a corresponding definition or example in the general medical database.

The invention may alternately be described as a method of using a medical database, the steps including: supplying a general medical database, the general medical database including information for at least three members of the group (i.e., Term Lookup, Drug Reference and Symbols) consisting of: medical terms, drugs, and entering specific medical information relative to at least one medical situation in a storage medium. Upon entry of the specific medical information, at least some terms in the specific medical information taken from a patient's medical record falling into each of the at least three members of group are part of specific medical information and are automatically referenced to definitions or examples of such terms in the general medical database such that selecting one of the referenced terms in the specific medical information causes the display of a corresponding definition or example in the general medical database. The general medical database and the specific medical information taken from medical records, medical forms, or situations such that information is entered using the selected template together constitute a customized database.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 7 is a screen display of a portion of the selection tree;

FIG. 8 is a screen display of significant information ("significant information" has a specific meaning as used herein and explained below);

FIG. 12 is an illustration of a term lookup, copy and paste feature with displays of general medical information being pasted into specific medical information sections;

FIGS. 14 and 15 are drug reference screens illustrating different features.

DETAILED DESCRIPTION

Figure 1:
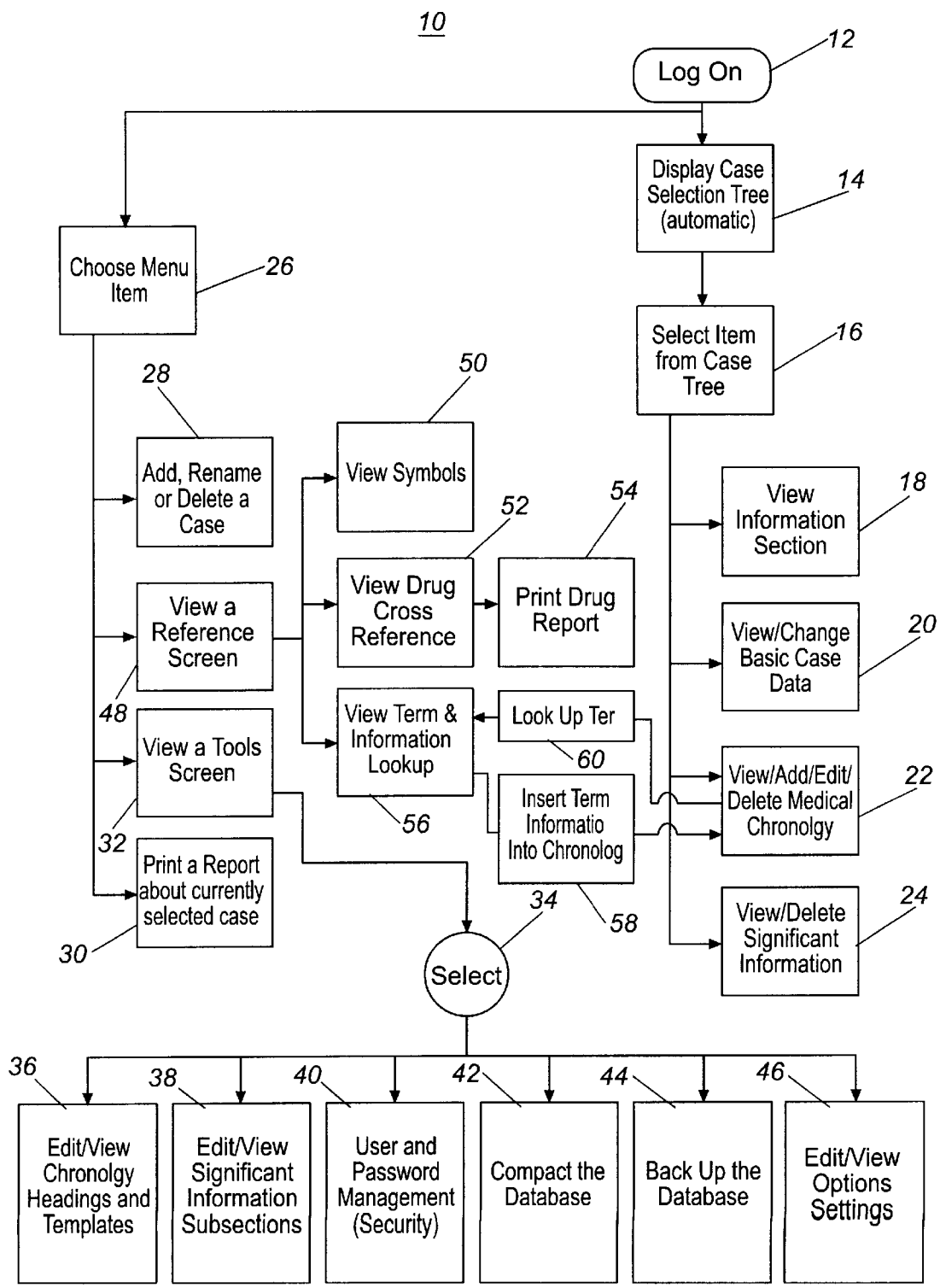
FIG. 1 is a simplified flowchart illustrating the method of the present invention.

FIG. 1 shows a basic flowchart 10 illustrating the operation of the present invention. It will be discussed in connection with various other FIGS. which correspond to screen displays or portions of screen displays generated by the program. At block 12, a log on or log in step is used. The database program of the present invention may, in known fashion, limit access to those with authorized user names and passwords. Block 14 causes the automatic display of a case selection tree illustrated as 114 in FIG. 2. For ease of understanding the screen displays or portions thereof will be numbered in the 100 series with the same last two digits as the corresponding block, if any, on the flowchart of FIG. 1. The case selection tree 114 is a common method of illustrating directories or files in the various WINDOWS (trademark of Microsoft) operating system. In this specific case, the tree 114 simply indicates that a user may select to display an Information Section. Alternately, the user can select an example case, a JB test case, or various subdirectories thereof as detailed below.

Upon the user selecting from the tree 114 corresponding to block 16, different items are displayed based on the selection.

Figure 2:
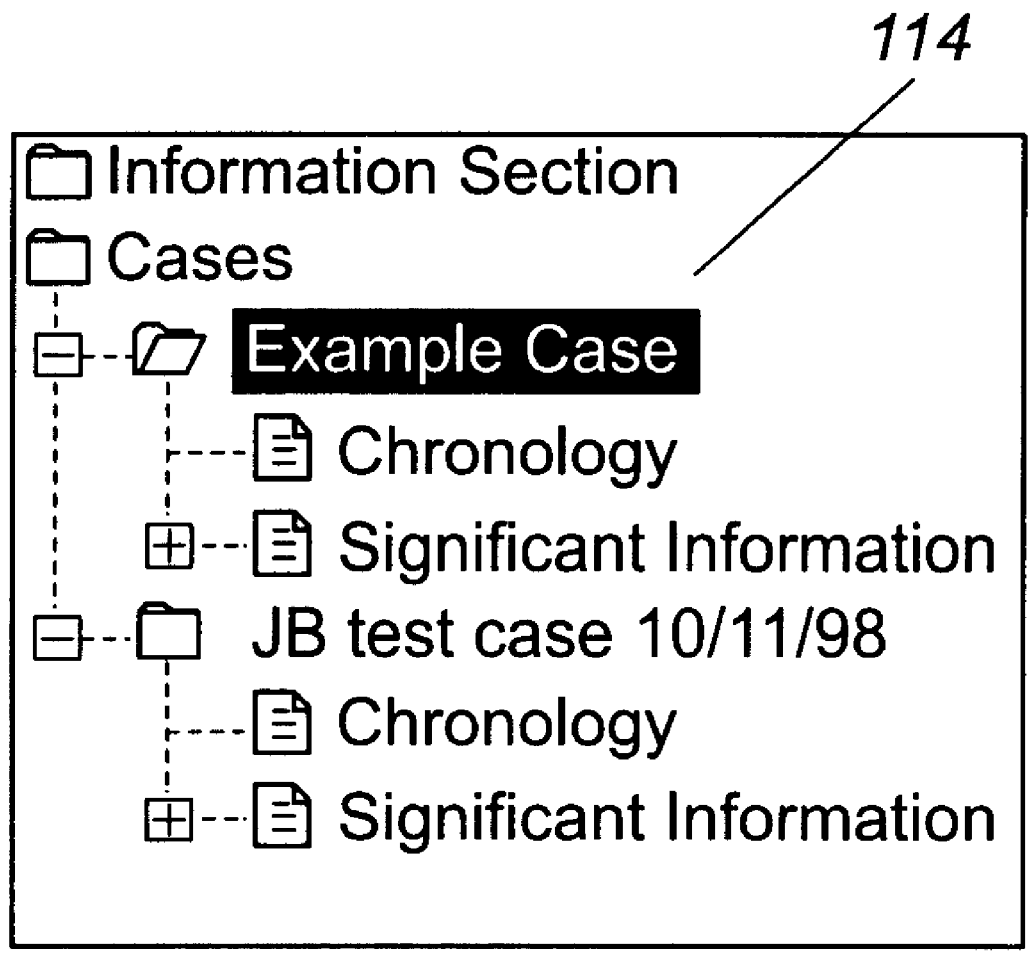
FIG. 2 is a screen display portion corresponding to a case selection tree used with the present invention.
Figure 3:
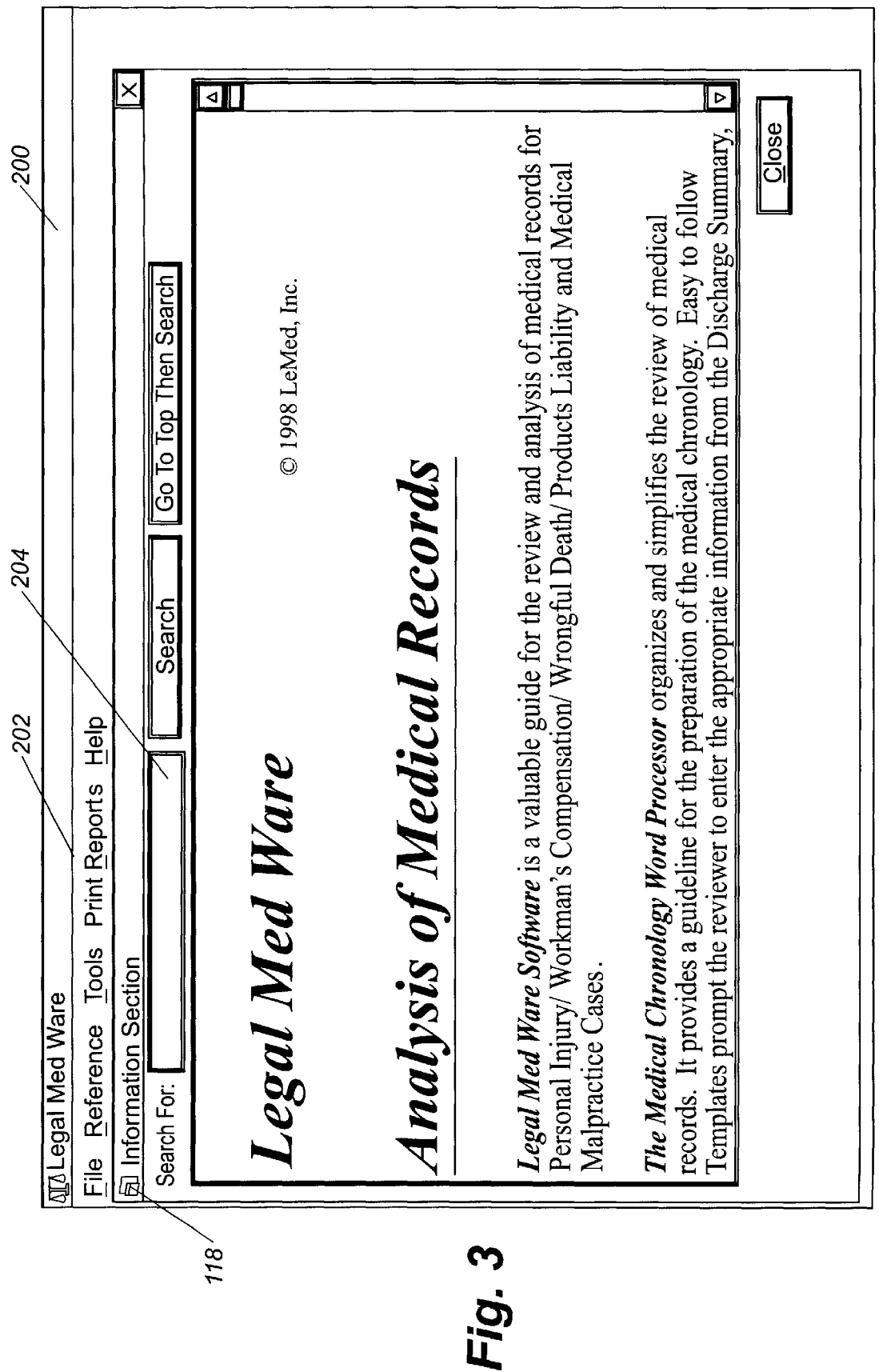
FIG. 3 is a screen display of the program window and and Information Section window of the present invention.

Block 18 corresponds to the user selecting the previously noted Information Section, a portion of which is shown at window 118 of FIG. 3. As shown, that portion 118 is within a program window 200 (labeled with a trademark LEGAL MED WARE for the program of the present invention) having various pull down commands 202. The program window 200 was not shown in FIG. 2 and will not be shown in other screen display FIGS. for ease of illustration, but it will be understood that the program window would normally appear with the other windows within it in known fashion.

Figure 4:
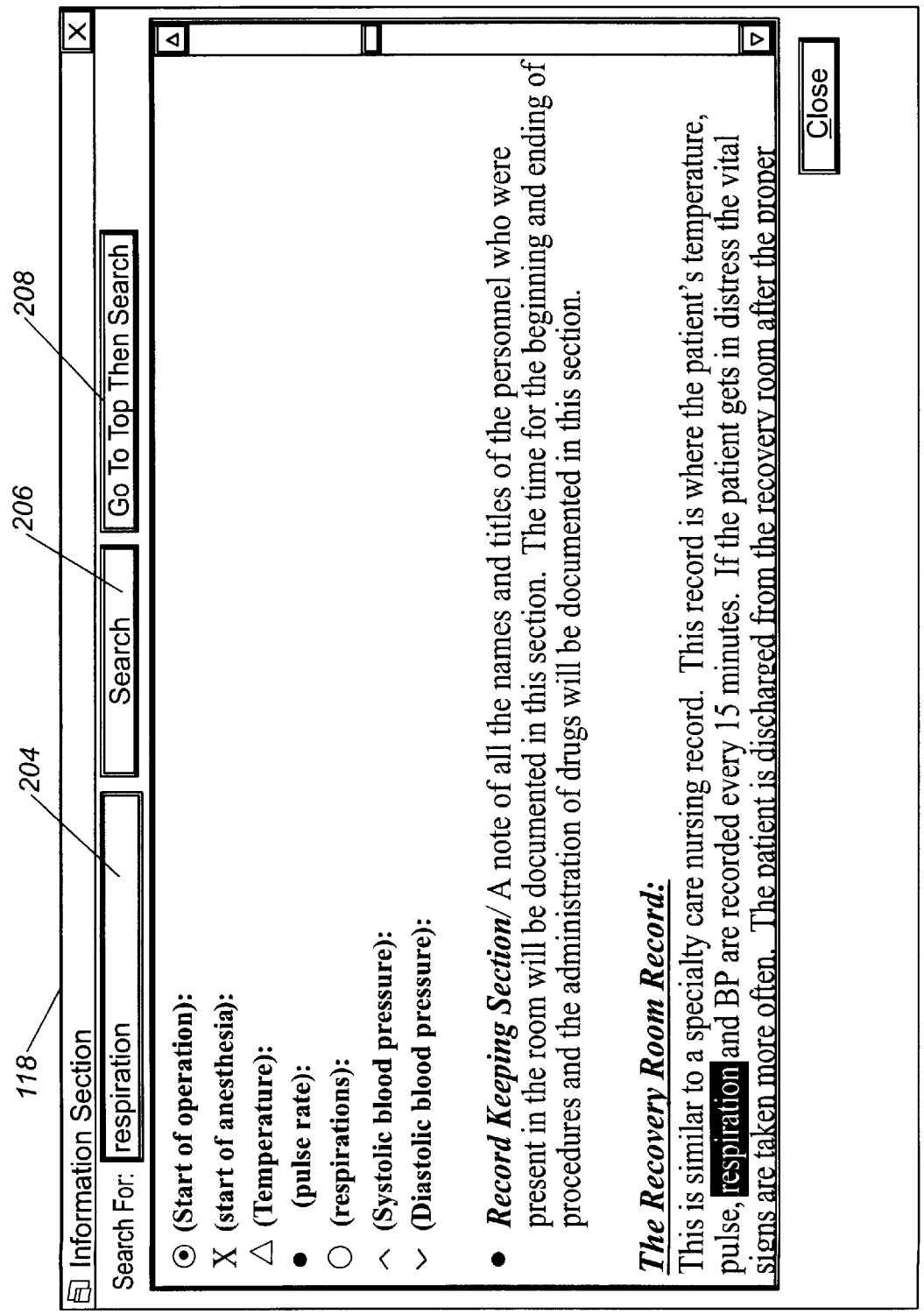
FIG. 4 is the screen display of the Information Section window after performing a search.

Continuing to view FIG. 3, but also viewing FIG. 4, a search field 204, search button 206, and "go to top then search" button 208 allows a user to easily locate terms in the Information Section. The example of FIG. 4 shows that typing "respiration" in the search field 204 and actuating the search button 206 automatically locates and highlights the search term ("respiration" in this case).

Figure 5:
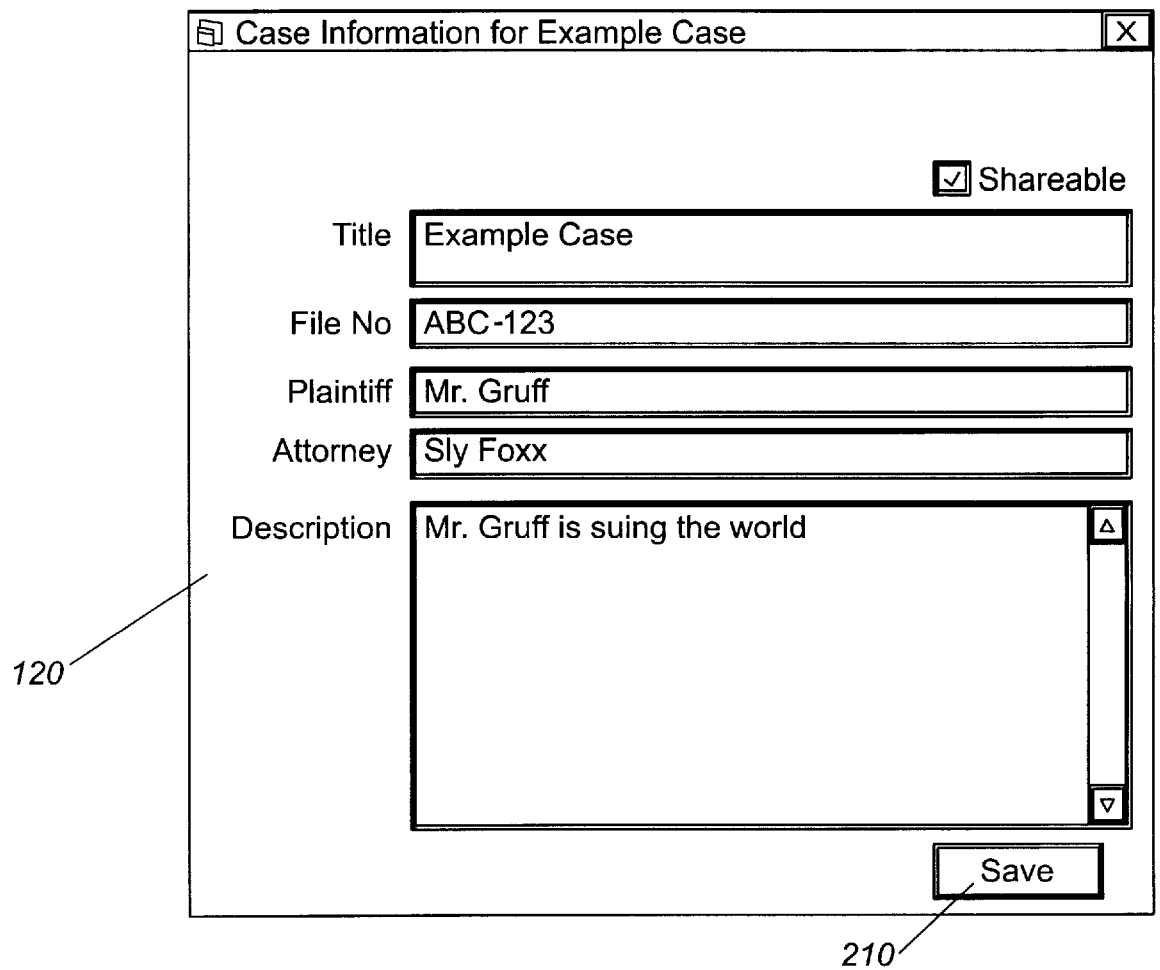
FIG. 5 is a screen display of case information.

Turning back to FIG. 1, upon selection of block 20, the basic case data 120 of FIG. 5 is displayed. FIG. 5 specifically shows the case data corresponding to the selection (as shown by highlighting in FIG. 2) of the example case. The fields of case data 120 are displayed and can be changed by typing in changes and clicking the save button 210.

Referring back momentarily to FIG. 3, the "file" pull down menu of menu bar 202 includes a "new case" command that displays a blank new case template similar to case data 120 of FIG. 5 such that data for a new case can be added and, upon saving, the tree 114 of FIG. 2 will be changed to add the new case.

Figure 6:
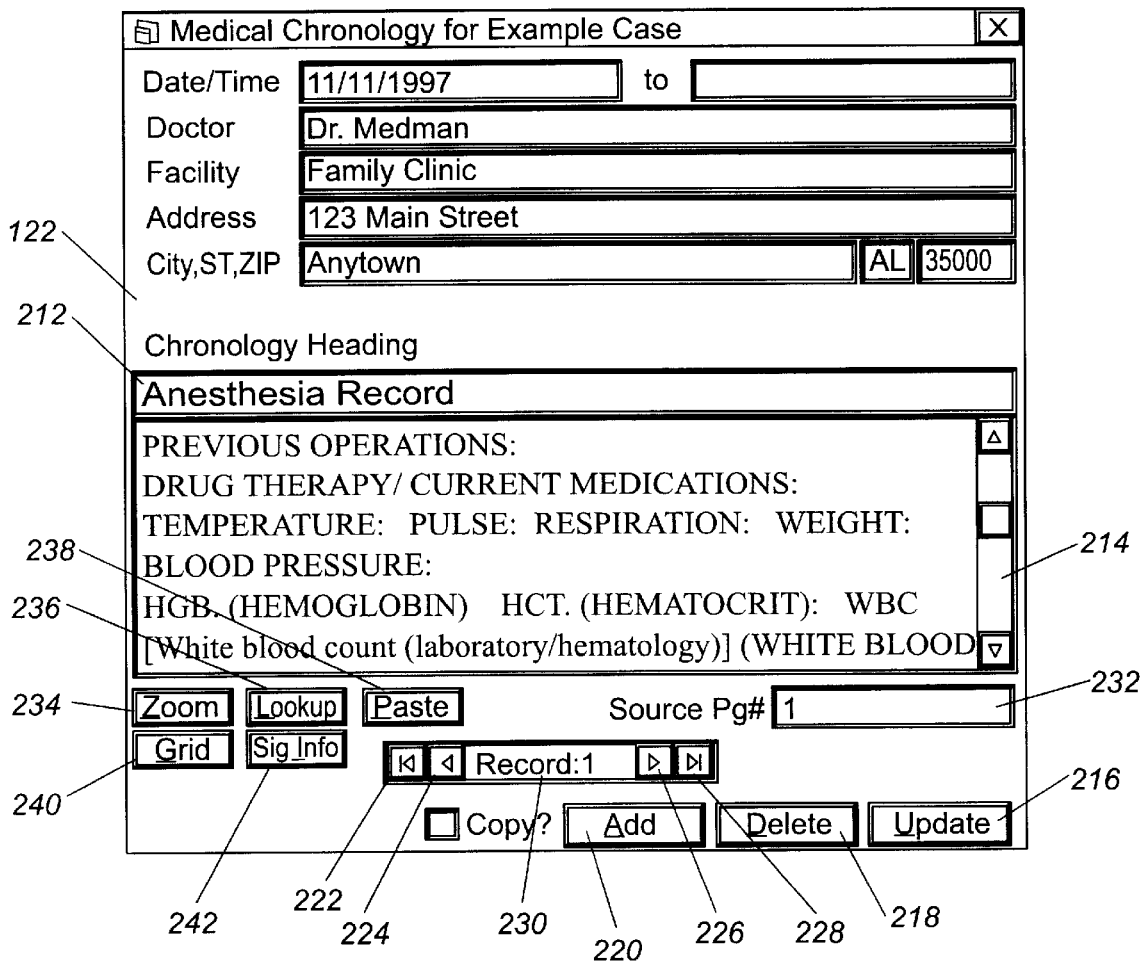
FIG. 6 is a screen display of a medical chronology record.

Block 22 of FIG. 1 brings up the display 122 of FIG. 6 which is one of a series of medical records corresponding to the medical chronology of a given case. The specific medical record displayed is an Anesthesia Record per title 212, but various other templates for different types of medical records are stored in the program such that data entry can be performed by less skilled workers and more skilled workers can concentrate on refining data previously entered. Display 122 has the illustrated fields at its top for a date, optional end date (if treatment extending over more than one day), doctor (or other medical practitioner such as dentist, registered nurse, etc.), facility, address, city, state, and zip code. Below title 212 are the various data categories which correspond to the given form and which may be scrolled using scroll bar 214.

New data can be typed into a medical chronology form such as 122 and clicking the update button 216. The delete button 218 deletes a particular record, whereas add button 220 brings up a blank form with title 212 selectable from a list (not shown) by operating a pull down menu (not shown) from adjacent 212. After selecting the type of record, the fields from the template for the selected form will appear below title 212 and next to scroll bar 214. The user can type in data and hit the update or enter button 216.

First record button 222, previous record button 224, next record button 226, and last record button 228 straddle record number display 230 and allow one to jump to a different record in a given chronology, whereas the page number of the source appears in display 232.

Zoom button 234 simply enlarges the view of the data in the given record. Lookup button 236 provides a particularly advantageous feature of looking up data from a general medical database in the manner described in detail below. Paste button 238 allows pasting of text or data onto the record after the material to be pasted has been copied elsewhere. Grid button 240 displays a grid showing the dates, document numbers, and doctors for the record shown at 122 as well as additional records. A user, such as a skilled reviewer of the data entered by others, can select (i.e., highlight with mouse or similar computer cursor device) information off the record and click on or actuate button 242 to automatically paste the highlighted material into a significant information file for the particular case.

Turning back to FIG. 1, block 24 allows one to view significant information. Specifically, FIG. 7 shows the a portion of the tree 114 of FIG. 2 with subdirectories of the significant information illustrated for the JB test case. The significant information may, for example, fall into one or more of the categories A through P on FIG. 7. The categories with a plus in front of their letter have entries, whereas the others do not (i.e., no entries in those categories for the particular case whose significant information is being viewed). By clicking on one of the categories having entries, such as "preexisting symptoms" in this case, the entries could be sequentially viewed with 124 displayed at the left side of the screen and the entries at the right side of the screen as shown for example in FIG. 8 which will be seen as a simplified display somewhat similar to the medical chronology form 122 of FIG. 6, but with fewer command buttons.

Again turning back to FIG. 1, log on block 12 allows one to go to choose menu item block 26. From there, block 28 allows adding a case, whereas alternate path block 30 allows printing of a report about a selected case, which may print a chronology by date or doctor or print the significant information for the case. View tools screen 32 goes to select 34 where one selects between chronology headings and templates 36, significant information subsections 38, password management 40, database compacting 42, database backup 44, and option settings 46. Block 48 leads to a reference screen such as view symbols block 50. Alternately, block 48 leads to view drug cross reference block 52 and, in turn, print drug report 54.

Figure 9:
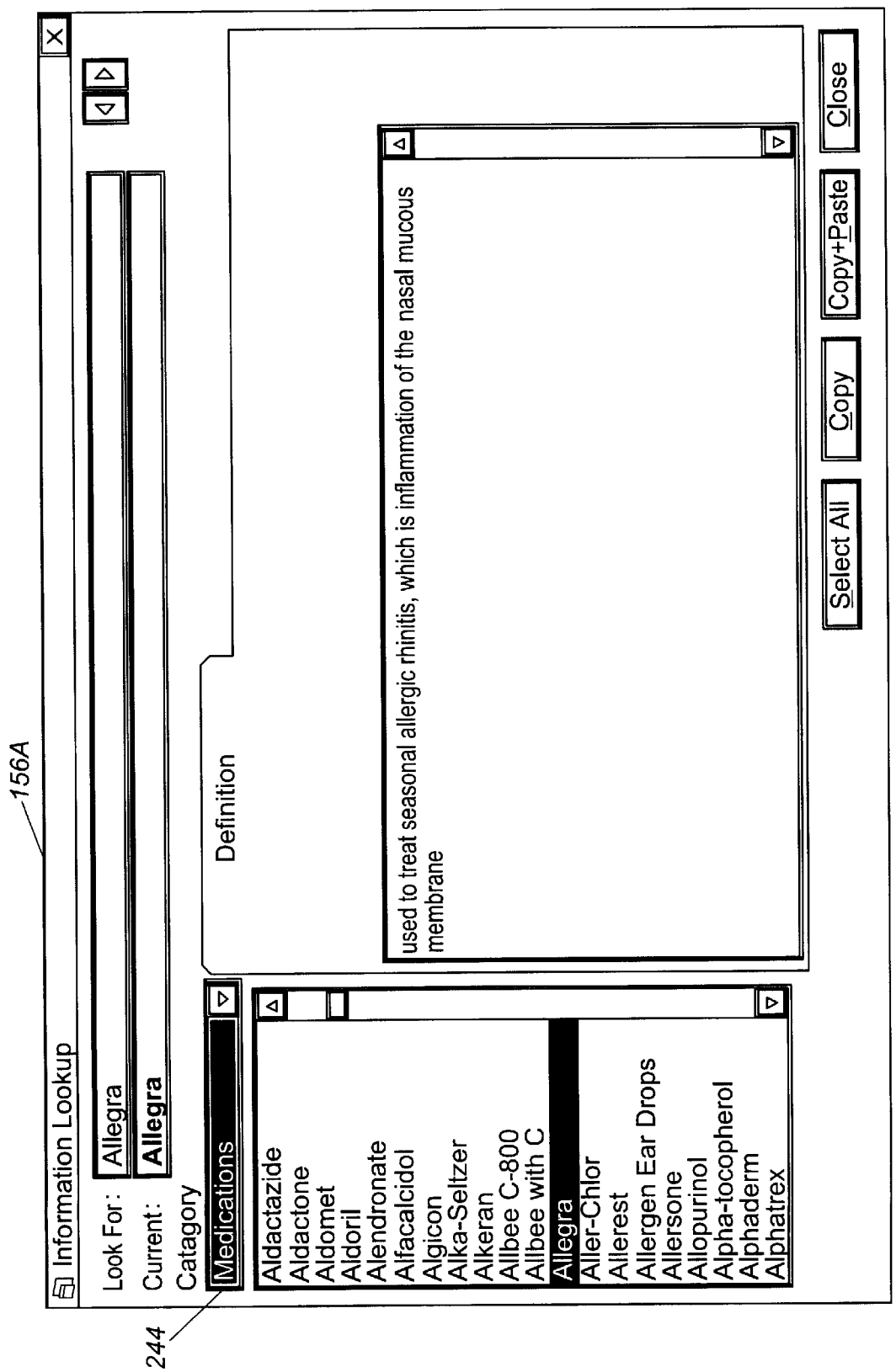
FIGS. 9 and 10 are screen displays of information lookup.
Figure 10:
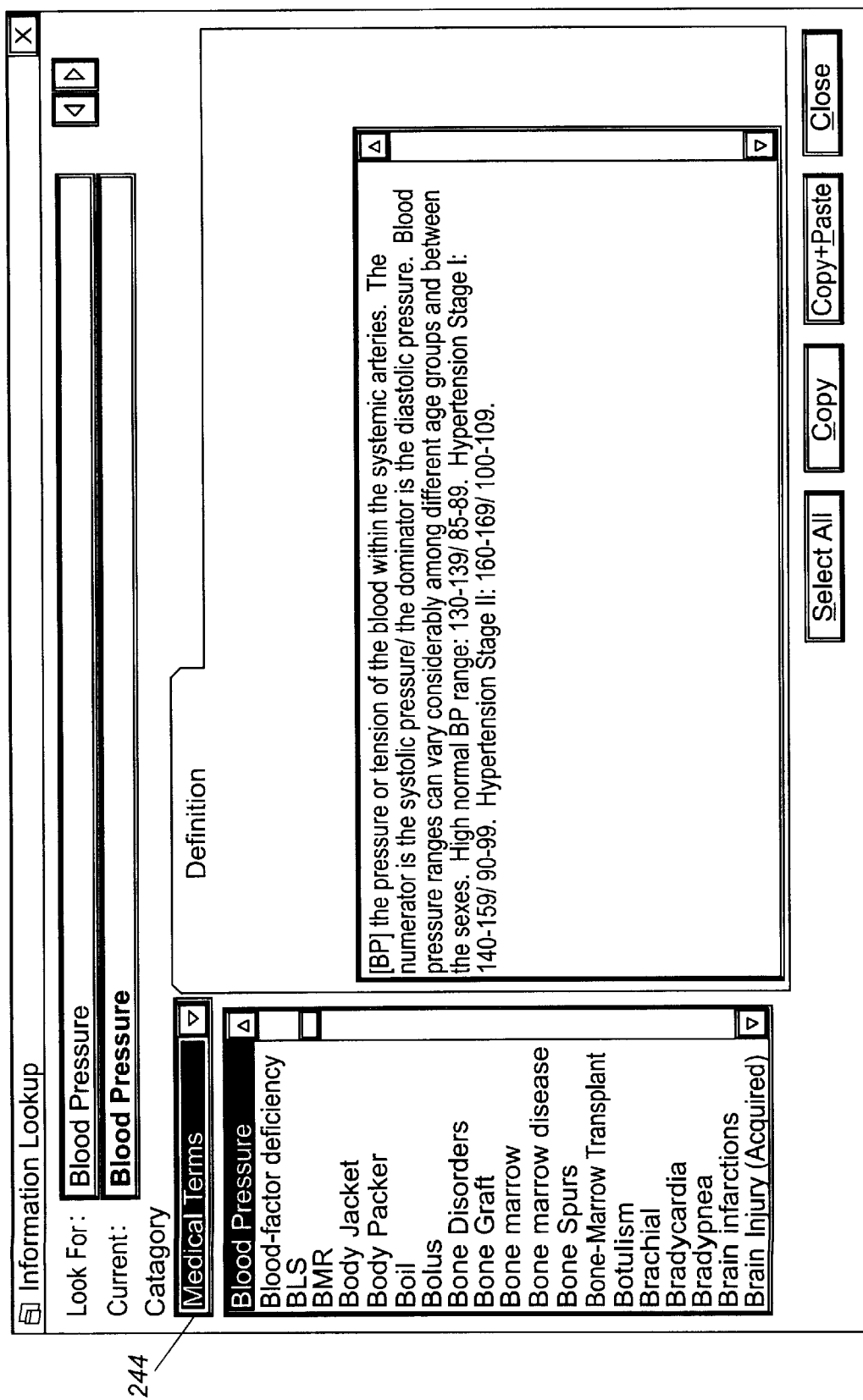

Block 48 alternately allows a user to go to "select a view term and information lookup" block 56. These blocks correspond to the displays 156A and 156B in FIGS. 9 and 10. Category selection field 244 allows one to select a category and search for information in that category such as medications in FIG. 9 and medical terms in FIG. 10.

Figure 11:
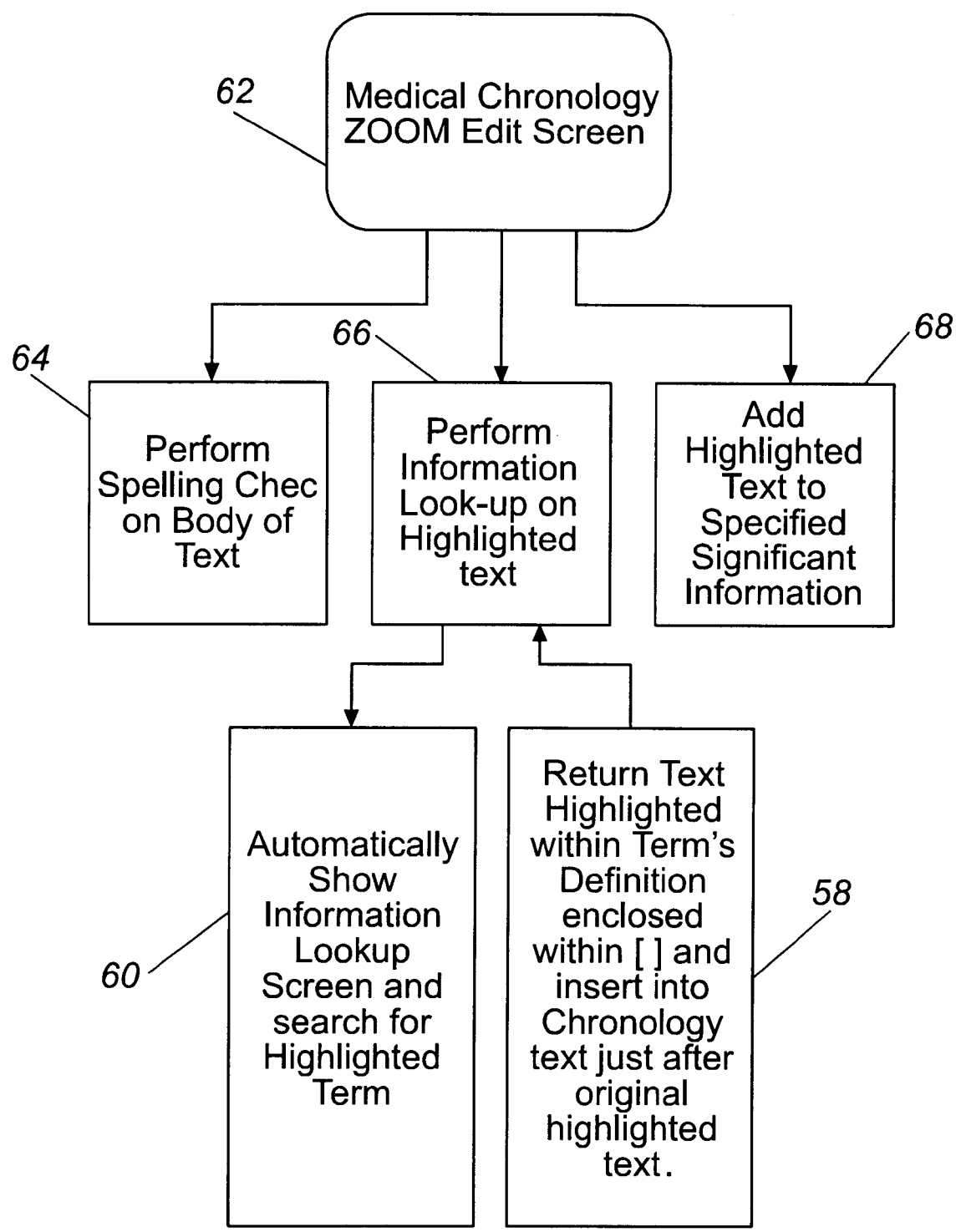
FIG. 11 is a simplified flowchart of a zoom screen operation of the present invention.
Figure 12:
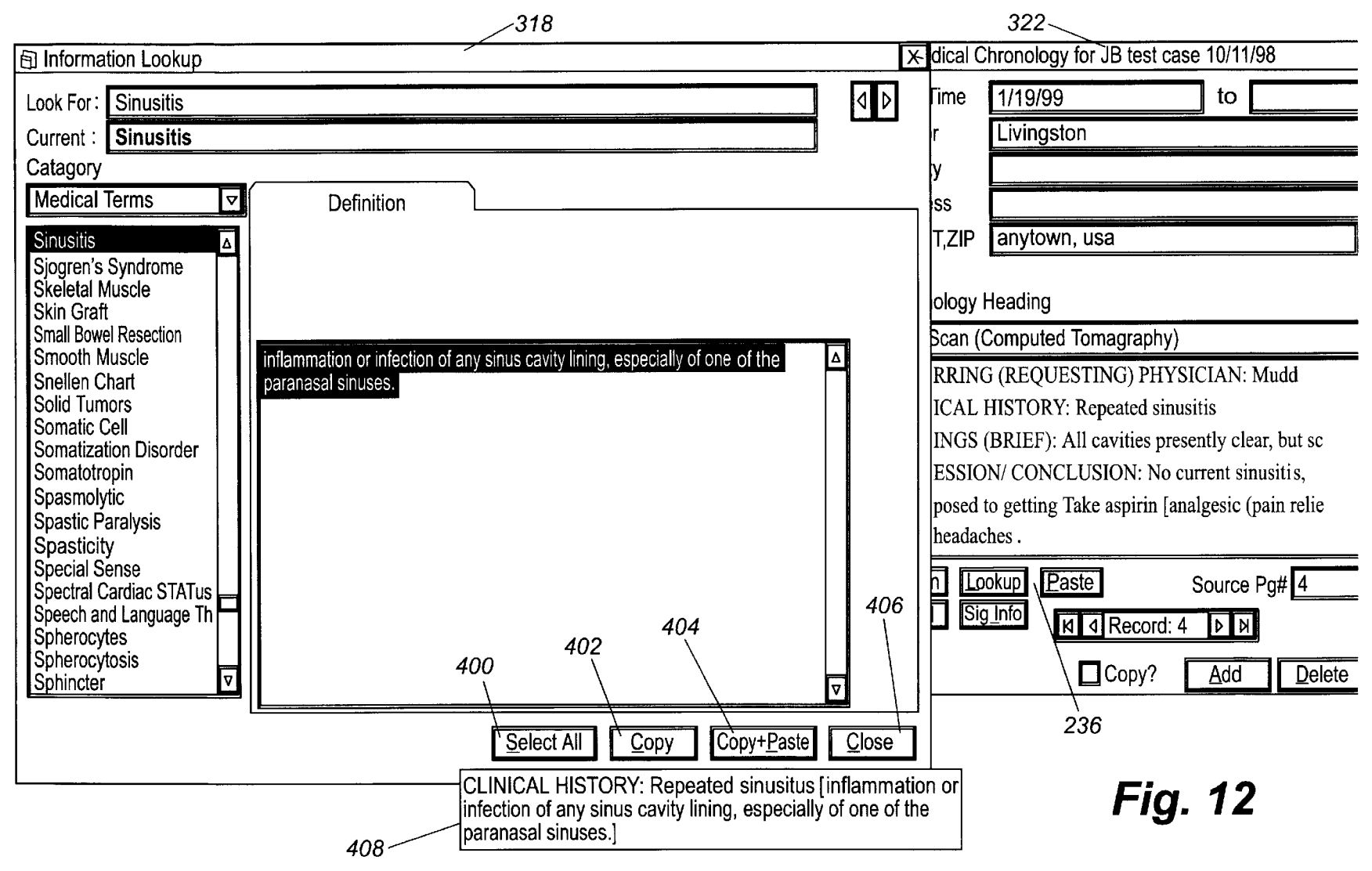

Blocks 58 and 60 of FIG. 1 provide a highly advantageous interaction between the general medical database (i.e., not specific to a particular case) corresponding to the information lookup and the specific medical information for a given case corresponding to block 22. Blocks 58 and 60 will be explained by also referencing FIGS. 11 and 12. However, other aspects of FIG. 11 will be described first. FIG. 11 shows the zoom edit screen block 62 (corresponding to zoom button 234 of FIG. 6) and may lead to spell check block 64. Alternately, block 62 leads to block 66 (corresponding to button 236 of FIG. 6) and beyond that to blocks 58 and 60 of FIG. 11, which are simply more detailed versions of blocks 58 and 60 of FIG. 1. These blocks will be explained in more detail with reference to FIG. 12 showing a medical chronology record display 322 (similar to record display 122 of FIG. 6). (Convention used in this specification has numbers in the 300 series corresponding to similar displays in the 100 series with the same last two digits.) Terms in the record of display 322 may be highlighted (selected by computer mouse) and actuation of lookup command button 236 will cause a display such as display 318. The term "sinusitis" was highlighted in display 322 such that, upon clicking the lookup button 236, information lookup display 318 automatically appears with a definition or examples of the term. In this case, "sinusitis" is defined. Display 318 has select all button 400, copy button 402, copy and paste button 404, and close button 406. After selecting all or part of the definition, copy and paste button 404 automatically copies and pastes the selected text from the general medical database into the displayed record of the medical chronology. In the example, button 404 inserts the sinusitis definition into the record of display 322. For ease of illustration, this insertion is simply illustrated by block 408 where a portion of the record has been changed by adding the text in the square brackets. In actual practice, the display 322 would change by having the sinusitis definition appear immediately after sinusitis in the display 322. The same copy and paste feature works for any term in a chronology record if the term is also in the information lookup portion which is the general medical database. This same copy and paste feature can work from the chronology record 322 directly or after giving the zoom command.

Figure 13:
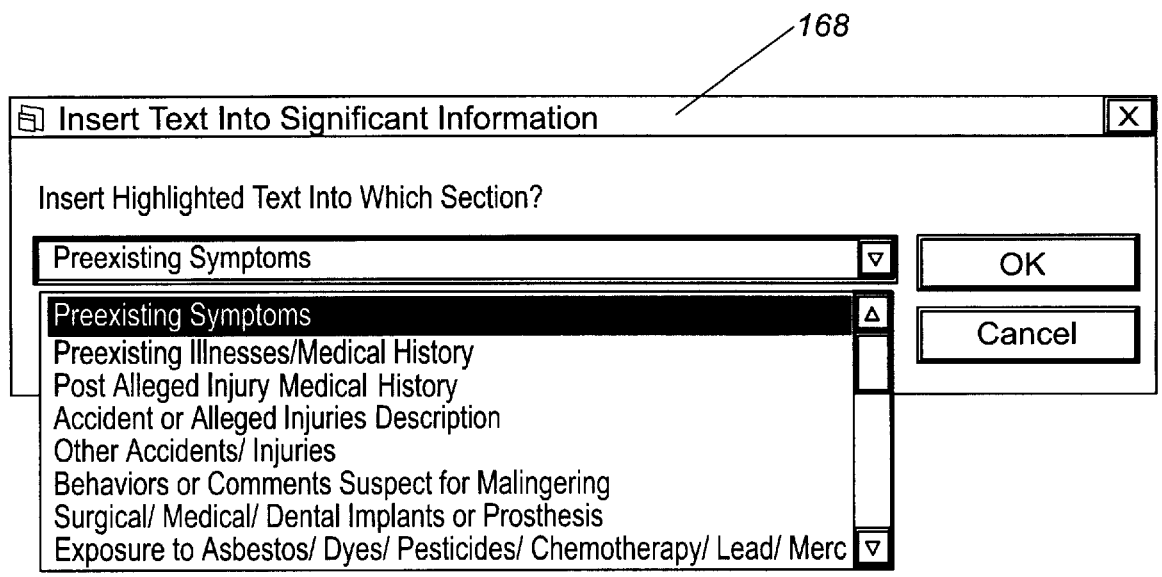
FIG. 13 is a significant information entry screen.

Block 68 of FIG. 11 allows adding highlighted information from a record to a significant information section. This same function, before going to the zoom display, can be accomplished by clicking significant information button 242 in FIG. 6. In either case, the display 168 of FIG. 13 appears and the user indicates which category of significant information should have the information copied from the chronology record.

Figure 14:
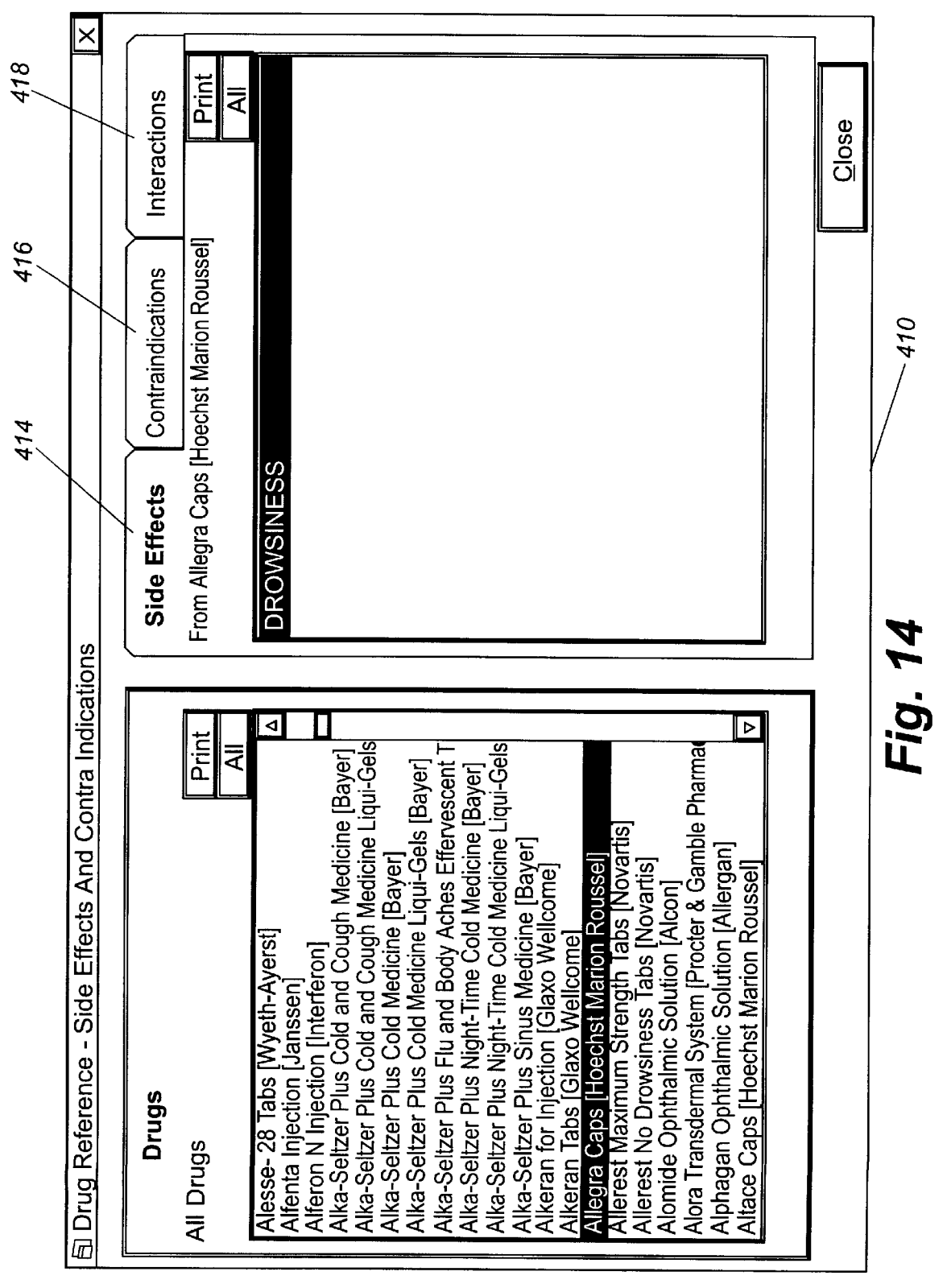

FIGS. 14 and 15 will be discussed with respect to drug reference displays 410 and 412 which can be accessed by the reference menu from menu bar 202 of FIG. 3. Initially all drugs are displayed on the left side of this window and all side effects on the right side. (Alternately, all contraindications or all interactions would be displayed on the right depending on which of leaves 414, 416, or 418 is selected.) In FIG. 14, the drug Allegra was selected on the left side such that the side effects are illustrated on the right side and are, in this case, "drowsiness." Highly advantageously, this program provides a two-way or double lookup feature. Upon seeing that Allegra has a side effect of drowsiness, one can click on the side effect (drowsiness in this case) such that display 412 appears where the side effect drowsiness is on the left and all drugs having that side effect are now displayed on the right.

Instead of initially selecting a drug, one could alternately select a side effect or a contraindication and the corresponding drugs would be displayed on the left. This quite sophisticated database access arrangement allows one to perform analysis that are quite useful in medical malpractice situations. Some examples may help explain this. Assume that an explanation for a given patient condition is of interest. The patient may have headaches and the program allows clicking on that side effect to show all medications that might cause that condition. If the patient has ringing in their ears, clicking on the drugs that the patient is taking may reveal if any could have caused that condition. If none appear to be the cause, one could then click on that side effect and follow up to determine if the patient left out other drugs that he or she was taking.

The various screen displays and flowcharts described above may be implemented by Visual Basic or some other program.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

Legal Med Ware Software is a valuable guide for the review and analysis of medical records for Personal Injury/Workman's Compensation/Wrongful Death/Products Liability and Medical Malpractice Cases.

The Medical Chronology Word Processor organizes and simplifies the review of medical records. It provides a guideline for the preparation of the medical chronology. Easy to follow Templates prompt the reviewer to enter the appropriate information from the Discharge Summary; Physician Order Sheet; Physician Progress Notes; Nurses Notes; Operative Report; History and Physical; Death Summary; Consult/Pathology Reports; X-rays; Laboratory Reports; Special Tests and Procedures etc.

The Significant Information Section provides a list of title entries that represent significant categories of information for the case. Highlight a word or phrase from the medical chronology and transfer it to the Significant Information screen under the appropriate title. The reviewer may create case specific headings or may choose from the list provided.

The Medical Database provides instant access to a wide variety of general medical definitions and information. The User may retrieve information concerning symptoms, diseases and differential diagnoses; normal laboratory values; medication indications, contraindications and side effects; and medical terms, symbols, abbreviations and acronyms.

Medical Database Table of Contents

Medical Terms

Symptoms, Diseases and Differential Diagnosis

Medical Symbols, Abbreviations and Acronyms

Normal Laboratory Values

Alcohol and Drug Toxicology

Medication Indications, Contraindications and Side Effects

Information Section for the Review of Medical Records and the Preparation of the Medical Chronology (Ideally the entire chart should be reviewed for relevant information. This may be a time consuming task, but it is essential for the complete analysis of a case).

1) Organizing Medical Records. (Organize/Number/Identify Documents)

Retain medical records with the cover page and in the order that they arrive from their source.

Number medical records.

Review the records to identify and briefly get familiar with the different kinds of medical records—Discharge Summary, History & Physical, Anesthesia Record, Operative Report, etc.

2) Reviewing Medical Records. (Medical Record Identification/Document Significance)

Discharge Summary:

The discharge summary is the optimal place to start your review because it provides the attending physicians' summary of the entire course of treatment. Normally, it is located at the front of the chart and must be dictated and transcribed. Since it is just a summary one should not rely on the discharge summary for a complete medical evaluation of the patient. Medication errors, accidents, injuries and complications may be omitted from the summary. In teaching hospitals the discharge summary may be assigned to residents or interns who may omit important issues because of inexperience and fatigue.

Physician Progress Notes:

Physician Progress notes are normally the most important part of the medical record because this is where the medical experts communicate to each other their diagnostic findings and medical opinions. Consulting physicians, medical students, interns, and junior residents may write in the physician's progress notes. Medical students' and interns' progress notes are very important. They may contain a more detailed explanation for a differential diagnosis of the patient□s illness.

Physician Progress Notes are Normally Very Difficult to Read.

Some helpful tips include:

Look for the illegible words to be duplicated in the progress notes to follow and then try to compare and decipher what they are.

Progress notes are normally full of medical symbols, acronyms and abbreviations. Look for them and let your Legal Med Ware medical database reveal their meaning.

Nurses' Notes:

Nurses must enter at least one note entry per eight-hour shift. The notes are usually handwritten and normally give an accurate around-the-clock account of the patient's condition. The notes give a medical chronology of the events of the patient's hospital stay. The nurse's notes are very important to the lawyer. The notes may contain statements that were made by the patient, family members, or physicians not found anywhere else in the record. Nurses are trained to record what they see and hear including any injuries the patient may have suffered.

Look for a sudden change in the patient's condition with no documented reason why.

Look for medication errors by noting the time that medications were administered. Be alert to medications administered too soon, without a physician order, or duplicated by another professional.

Look for handwriting discrepancies—for example, if a particular nurse always enters her notes in an apparent hurried handwriting style and then you notice suddenly a very organized disciplined style of handwriting—read very carefully the notes before and after for any kind of incident.

A patient may ask for pain medication every 3–4 hours and tell the physician the pain is unbearable. The nurses notes may document "patient smiling, joking with nurses" "talks on the telephone constantly", "friends visit, the patient is laughing and appears to be in good spirits".

Psychiatry Consults:

Psychiatrists, psychologists and psychiatric social workers may perform psychiatric consultations. They may enter a note about the consult in the patient's chart but a comprehensive note may be written or dictated and filed in the psychiatry department records of the hospital. You may have to obtain those records via the psychiatry department.

Operative/Surgical Report:

The surgeon who performed the surgery or a senior resident may dictate the operative report. The operative report must include the preoperative diagnosis, the description of the skin incision, a detailed description of the operative site and what was done, description of the suture closure of the wound, the postoperative diagnosis and the condition of the patient at the completion of the operation. If any of the parts are missing one should follow up to determine why.

Look for Discrepancies:

Look for surgical hardware and surgical implant product numbers that do not match the other surgical notes.

Does the patient have a documented allergy to the type of suture material, bandage, tape or medication used in the surgery?

The Anesthesia Record:

The anesthesia record is usually hard to interpret. It can be evaluated easier by breaking it down into sections.

The Patient Information Section/This section will give information that will help to accurately identify the patient (patient's name and room number).

Pre-anesthesia Data Section/This section will most likely have Chest x-ray, EKG, and CBC (complete blood count) results. The section could reveal a low hemoglobin value, which could be indicative of anemia and a high WBC (white blood count) value, which could be indicative of a possible preexisting infection. This section will also include any allergies and a list of the patient's current medications. Patients usually are more forthcoming with an Anesthesiologist so this section may contain information the patient has not provided to others. For example the patient may admit to an Anesthesiologist significant information such as any illegal drug use or drug abuse. Significant facts about a patient's past and present medical/surgical history will be noted in this section. Look for any medical/surgical history that may be related to a previous accident or injury.

Events Section/All events are written and numbered. Then the corresponding numbers are written below the graphic chart for comparing information about what happened during surgery and when it happened.

Medication Section/All medications that are administered to the patient (including gases), are normally recorded in the upper left-hand side of the graphic chart. The drug dose is noted in the appropriate time slot across the graphic chart.

Monitoring Section/Special machines have alarms that monitor the patient for temperature, oxygen and carbon dioxide content and EKG recordings.

Some symbols used in the Anesthesia Record are:

(Start of operation):

X (start of anesthesia):

(Temperature):

• (pulse rate):

○ (respirations):

(Systolic blood pressure):

(Diastolic blood pressure):

Record Keeping Section/A note of all the names and titles of the personnel who were present in the room will be documented in this section. The time for the beginning and ending of procedures and the administration of drugs will be documented in this section.

The Recovery Room Record:

This is similar to a specialty care nursing record. This record is where the patient's temperature, pulse, respiration and BP are recorded every 15 minutes. If the patient gets in distress the vital signs are taken more often. The patient is discharged from the recovery room after the proper assessment and stabilization of the patient's vital signs.

Incident Report:

Incident reports are difficult if not impossible to obtain. They will describe a patient incident/injury and detail what happened—when it happened—who was there and what treatment was given.

Incident reports do not normally stay with the patient's medical records. If there was an injury or medication error noted in the nurses notes—an incident report was probably completed and filed in the administrative office of the hospital.

Note: Check medication records and nurses notes for medications (especially mind altering) that may have been administered prior to the incident/accident. (* Was the patient sedated 60 minutes before falling out of bed?)

Intraoperative Nursing Care Record:

The Intraoperative Nursing Care Record may include the sponge and instrument count. The sponge and instrument count is carried out before the operation begins, once just before closure, and again after closure. This record is not always a part of the patient's chart and may have to be requested separately. Nurses will sign off whether the count was correct or incorrect. A retained surgical sponge (gossypiboma) can be prevented if the count is reported incorrect and the retained sponge is retrieved before closure of the wound. Radiopaque markers are normally on surgical sponges so their appearances can be well documented. A radiopaque marker may be distorted by folding or twisting, or damaged over time. Retained sponges are practically impossible to diagnose without radiopaque markers.

Surgical Device Identification (prosthesis/surgical hardware/implant/pacemaker) may be located in the Intraoperative Nursing Care Record. The type of device and lot number should be documented there.

Records Related Specifically to Nursing:

Graphic Chart/A chart (summary) of the patient's temperature, pulse, respiration's and blood pressure.

Nurse's Medication Record/A record (summary) of the drugs to be given to the patient. The nurse enters her initials and then notes the route, dose and time the medication was given.

Intake & Output Chart/A record (summary) of the amounts of fluids taken by the patient (by mouth and intravenously) and also a record of the quantities of fluids put out by the body (vomiting, diarrhea and urination). This record will be a useful aide in calculating the amount of drugs or alcohol in the blood of a trauma/accident victim at the time of drug testing. If a victim's blood is diluted by the administration of IV fluids prior to a testing for alcohol and drug use, the test will be suspect for being inaccurate. This chart may help detect any fluid or IV fluid overload and any decreased renal function or renal failure.

Laboratory and Diagnostic Tests:

These include various kinds of blood work, bacteriological studies, cytology reports, pathology reports and diagnostic tests. The normal values will vary from hospital to hospital and laboratory to laboratory.

3) Standard of Care Documents.

Morbidity/Mortality Committee:

A hospital may have a morbidity/mortality committee. The committee may evaluate deaths and comment on correctable measures and suggestions for the improvement of patient care.

Procedures Manuals:

All hospital departments (radiology, nursing, anesthesia, pharmacy and respiratory therapy etc.) have procedure manuals. These are very important documents for the standards of care for a patient. The manuals should have training requirements for personnel who perform certain procedures. The manuals may have questions to ask the patient before beginning a procedure. Proper technique for procedures will be noted in the manual. Normally hospital personnel are required to review the manual and document the review. All personnel normally must read any new or revised procedures.

Utilization Review/Quality of Care Review:

These are evaluative standard of care studies performed by hospital departments or agencies separate from the hospital.

Incident Reports/Medication Incident Reports:

Accidents, patient injuries, medication errors and treatment errors will be documented on these reports. These documents are very useful to lawyers but because of privilege statutes may be very difficult to obtain.

Pharmacy Patient Medication Sheets:

These are patient medication records that are not filed in the patient's medical record, but are kept in the pharmacy. These documents normally contain a complete summary of all of the medications that were taken by the patient.

Death Summary:

This document is similar to a discharge summary. The death summary is very important and may have valuable information for the lawyer because it may indicate other factors that contributed to the patient's death. This document may or may not be located in the patient's medical records.

Autopsy:

An autopsy report is an important document for a patient's COD [cause of death].

Note: A patient's cause of death may be listed as "Renal Failure", but "Renal Failure" may be secondary to alcoholism, drug toxicity, allergic reaction, etc.

4) Analyzing Medical Information.

(Compare symptoms, diagnoses, diseases, laboratory values, pathology reports, special tests and radiology reports)

Defense: Look for other causes of the alleged injury. Compare the symptoms, diagnoses, diseases, medications, laboratory values, pathology reports, special tests and radiology reports to ascertain other causes or contributing factors for the alleged injury.

Plaintiff: Look for symptoms, diagnoses, diseases, medications, laboratory values, pathology reports, special tests and radiology reports that confirm or substantiate a claim for the alleged injury.

5) To Begin

Read the Medical Records.

Go to your Legal Med Ware Software.

Go to "Building a Medical Chronology".

Go to the Case Information screen and fill it out.

Go to the Medical Chronology screen and begin.

First set of fields (reviewer fills out)

Second field (software provides Chronology Headings, or the User may create Chronology Headings)

EXAMPLE

Office Visit:

Third field (Chronology Entry field. The software provides Chronology Heading Templates for this field)

EXAMPLE

Symptoms:

Laboratory Results:

X-rays and Special Procedures:

Diagnosis:

Medication and Treatment:

In the first field fill in the Date, Time (if applicable), Doctor's Name, Medical Provider, and Address.

EXAMPLE

Mar. 12, 1997 7:15 AM Dr. Joe Blow/Regional Medical Center/407 Park Lane/Albany, N.Y. 35217

In the second field choose either from the available Chronology Headings, or fill in the kind of medical record (Chronology Heading) you want to summarize, (Discharge Summary/Consult/Physical Therapy Notes, etc).

Software Heading Template:

EXAMPLE

Discharge Summary:

In the third field either fill out the Chronology Heading Templates, or prepare a summary of the medical record document.

Software Chronology Heading Template:

EXAMPLE

Admitting Diagnosis:

Hospital Course:

Consults:

Laboratory and X-ray Findings:

Special Procedures:

Operations:

Discharge Medications:

Discharge Diagnosis:

Discharge Instructions/Plan:

(Source Pg. #)

Enter the source page number (Source Pg. #).

Follow the software Chronology Headings and Chronology Heading Templates for the other medical records in the case, or create your own summary format.

When you see a laboratory value, medical term, symbol, abbreviation, medication and so on, that you are not familiar with—Highlight the term, or symbol, review the displayed screen, select and then paste your choice in the medical chronology (Chronology Entry).

When you see a word or phrase that you wish to enter in the Significant Information section—Highlight the word, or phrase and then select from the Significant Information Subsections, or create your own.

Significant Information Subsections (The reviewer may accept these titles or change them as desired)

a. Preexisting Symptoms
b. Preexisting Illnesses/Medical History
c. Post Alleged Injury Medical History
d. Accident or Alleged Injury Description
e. Other Accidents/Injuries
f. Behaviors or Comments Suspect for Malingering
g. Surgical/Medical/Dental Implants or Prosthesis
h. Exposure to Asbestosis/Dyes/Pesticides/Chemotherapy/Lead/Mercury/Plastics or Silicone
i. Alcohol/Drug/Tobacco Usage
j. Mental/Emotional History
k. Patient Non-Compliance
l. Other Legal Actions/Worker's Compensation Claims
m. Activity Level/Hobbies and Special Interests
n. Mental Cognizance
0. Medications
p. Drug/Alcohol [ETOH] Testing
q. Allergies
r. Educational/Employment History
s. Social History
t. Family Medical History
u. Case Discrepancies
v. Possible Defense Experts
w. Possible Plaintiff Experts
x. Medical Records Missing/Documents to Request 6) Preparing a Document for Expert Review, Deposition, Mediation and Trial.

Print the Significant Information section of the software, which will have a comprehensive outlined chronology of the significant facts of the patient's medical records. The Significant Information section is the heart of the medical chronology.

Print all of the medical chronology for the physicians pertinent to the Expert Review, Deposition, Mediation or Trial, (See Print Reports, Medical Chronology by Doctor). The reviewer can easily perform a search by the doctor's name and the software will collect, format and copy all of those documents for quick and effortless reference.

Please read the Help File for instructions in the use of Legal Med Ware.

For a quick start begin with "Building a Medical Chronology" below:

Building a Medical Chronology

To Begin:

Log in and the software "Information Section" will automatically be displayed if the User has the "Show Info at Startup" checked in "Options" under the "Tools" menu.

If the User did not have "Options" checked, clicking the "Information Section" on the left side of the screen may launch the "Information Section". The "Information Section" is a valuable part of the software. READ ALL of the "Information Section" before using the software. The User may refer to the "Information Section" often while working up a case. Specific topics (Example: "Nurses Notes") may be located by typing in the search field located above the screen. The "Information Section" prepares the User for the review of medical records and application of Legal Med Ware software.

The Following Steps Guide the Application of "Legal Med Ware"

Step 1: Starting A New Case:

1) From the File Menu on the Main Screen, select "New Case". The Case Tree will appear to the left of the screen with three new entries.

2) The first entry is highlighted "New Case". Type in the name that the User will use for the case (Example: Jones vs. Jackson Medical) and press Enter, and the case will be named.

3) The second entry is called "Chronology".

4) The third entry is called "Significant Information". Listed under "Significant Information", the User will find a list of lettered titles that are "Significant Information Subsections."

Step 2: Filling In The Case Information Screen:

1) After the User has named the case, look for the "Case Information for (new case name)" screen located to the right of the main screen.

2) Check the "Shareable" checkbox if the User would like for others in the multiple User setup to view and change the contents of the case.

3) Fill In The Following Data Fields:

"File No.": numerical reference/client billing number for the case.

"Plaintiff": name of the plaintiff.

"Attorney": name of the attorney handling the case.

"Description": brief synopsis of the case.

4) Once the User has completed filling in the "Case Information for New Case" screen, click on the Save button at the bottom of the screen and the case will be stored in the database.

Step 3: Creating The Chronology Entries For The "Medical Chronology" Screen (Medical Chronology Word Processor):

1) To create the Chronology Entries for the Medical Chronology, click on the word "Chronology" under the case's name located in the Case Tree screen positioned to the left of the main screen. Immediately after clicking the word "Chronology", the "Medical Chronology" screen will take the place of the "Case Information" screen.

2) FIRST THE USER MUST CLICK the "Add" button locked at the bottom of the screen. The Add, Delete, and Update buttons will be replaced with "Save" and "Cancel" buttons. This allows the User to add a Chronology Heading and Chronology Entry. First the User must type the requested information in the data fields, and click the tab to the right side of the Chronology Heading bar for the selection of the Chronology Heading. The User must click "Save" to keep the selection, or "Cancel" to cancel and exit the selection. The Copy checkbox will be hidden as will the special function buttons, and the Record # Tabs before the selection of "Save" or "Cancel". The "Update" button saves any added information to the Medical Chronology database. The "Delete" button deletes the Chronology Heading and Chronology Entry.

Notes About Fields/Buttons:

a) The Date/Time field will convert military time (24-hour time format) to AM/PM format if entered properly.

b) The "Chronology Entry" field has "Heading Templates" (mentioned in the Information Section), which may be accessed by clicking the tab to the right of the "Chronology Heading". A dropdown list will display a selection of "Chronology Headings" (Example: Discharge Summary, Nurses Notes, Anesthesia Record, etc.).

If the User wishes to add a "Chronology Heading" different from those provided in the dropdown list, simply click "Chronology Headings" located under the "Tools" menu. Click the "Add" button and type in the desired Chronology Heading (Example: Letter to Dr. Cooper:), and click "Update" and "Close".

If the User clicks the "Use Templates" option located under the Tools menu, an easy to follow, "Heading Template" will be placed in the "Chronology Entry" field (located just below the "Chronology Heading". The Heading Templates prompt the reviewer to enter the appropriate information from the Discharge Summary, Physician Order Sheet, Physician Progress Notes, etc.

c) The Chronology Entry field is a Rich Text field. A Rich Text field allows the User to change the text to Bold, Italic, or Underline by clicking the appropriate buttons. If the User wants to use the Bold, Italic or Underline buttons to edit the chronology, click the "Zoom" button located on the "Medical Chronology" screen.

d) Description Of The 5 Buttons Located Below The Source Text Field:

"Zoom": gives access to a full screen. On this screen the User may use the "Bold", "Italic", "Underline" or "Spellchk": buttons to edit the chronology, and have the benefits of a large screen. When ready to exit the "Zoom": screen click "OK".

"Grid": reveals a list of all "Chronology Entries" for the case that the User is currently accessing.

"Lookup": permits the User to search the database for medical information about the highlighted medical term or phrase from the Source Text (Medical Chronology). Just click the mouse on the term or phrase, and hold down the left mouse button, and move the cursor to highlight the term or phrase, then click the "Lookup" button and the software will attempt to find the word or term in the medical database. The "Drug Reference" and "Symbols" sections are not accessible through the "Lookup" search. The User must access those databases by the "Reference" menu. The "Drug Reference" offers a list of side effects and contraindications. The drugs that may cause the listed side effects and contraindications are alphabetically listed to the left of the screen. The "Drug Reference", and "Symbols" screens may be used for quick reference, or may be printed. "Sig. Info": permits the User to transfer highlighted words or phrases to the "Significant Information" section, which provides a list of Significant Information Subsections that represent significant categories of information for the case. Highlight a word or phrase from the Chronology Entry (Medical Chronology) and transfer it to the "Significant Information" section under the appropriate "Significant Information Subsection".

After the User has highlighted the word or phrase and clicked "Sig. Info" the "Insert Text Into Significant Information" Screen appears and the User will be prompted to choose from several "Significant Information Subsection" titles. Choose the appropriate Significant Information Subsection and click "OK", and the information will be stored under that Significant Information Subsection.

To add a new Significant Information Subsection (one that is not listed) for a new case, click the "Tool" menu, and select "Significant Information Subsections", and the "Significant Information Subsection" screen will be displayed. Click the "Add" button and type the name of the new Subsection in the empty space at the bottom of the table. Click "Save", close the screen and the new "Significant Information Subsection" will be ready for the next new case.

To add a new Significant Information Subsection (one that is not listed) to an existing case, click on the case to make it current, and then go to the File menu and select "Add New Significant Information Subsection". The highlighted "New Significant Information Subsection" will be located on the bottom line of the Significant Information Case Tree. Type a capital letter in the highlighted area (the letter that follows the last letter entered: Example: X after W, or AA after Z), before the new entry is typed, and press Enter on the computer keyboard, and the new Significant Information Subsection is ready for use. "Paste": permits "Copied" information to be "Pasted" in the area where the cursor has been positioned in the Chronology Entry field (Medical Chronology).

3) After the User has completed filling out the requested information for the "Heading Template" fields, other significant medical information found in the medical record may be entered. If the User has Medical Abbreviations, Medical Terms, Medications, Specific Diseases or Laboratory Values, etc. that need to be searched for in the medical data base, the User may highlight the term or phrase and click the "Lookup" button (mentioned above) located on the "Medical Chronology" screen. If the medical item is available in the medical database, the "Information Lookup" screen will appear with the highlighted medical item located to the left of the screen, and the requested medical information displayed to the right of the screen. The User may click the "Select All" button, and "Copy & Paste", or the "Copy" button to transfer the information to the Chronology Entry (Medical Chronology). If the User wishes to transfer any significant information to the "Significant Information" section (mentioned above), the User may do so. After the User has completed the "Chronology Entry", make sure the "Source Pg. #" (numbered medical record's number) has been entered.

THE USER MUST CLICK the "Update" button to save the data that has just been entered.

There is a time saving "Copy" checkbox located on the "Medical Chronology" screen after the first entry has been complete d and updated. The User may wish to check "Copy" so the software will automatically inherit the entire Doctor, Facility, and Address information from the current entry. The User will need to click "Copy" before clicking "Add" to add another chronology entry. This is very useful when the User has several "Chronology Entries" from the same doctor or facility.

4) The User may review the "Significant Information Items". After entering information into several of the "Significant Information" Subsections, the User may wish to view the items entered by clicking the "plus sign" to the left of the words "Significant Information" on the Case Tree. The list of Significant Information Subsections will appear. If the User clicks t he Significant Information Subsections again, they will collapse and disappear. Significant Information Subsections that have at least one entry will have a plus sign next to it. To view the items in a Significant Information Subsection, click the Significant Information Subsection (Example: "Preexisting Symptoms") and the "Significant Information Items" screen appears. The User may delete entries from that screen.

5) To add another "Chronology Entry" (assuming the User has already "Updated" the previous entry), THE USER MUST FIRST CLICK the "Add" button positioned at the bottom of the screen, and continue with the same process given in "Step 3: Number 2" above.

6) As the User adds Chronology Entries, the "Record #" will increase with each new Chronology Heading and Chronology Entry. The "Record #" Tabs are located just above the "Add" and "Copy". The User may scroll/move through the Chronology Entries by clicking the arrow-like Tabs on the sides of the "Record #".

7) The User may save Case Information, Medical Chronology, and Significant Information documents by going to the File menu, and clicking on "Save As". The documents can be saved in Rich Text format [*.rtf] on the hard drive or a floppy disc.

The "Save As" feature is recommended for:

Saving a copy of a case on a floppy disc to mail to the client, or other Firms.

Saving to a copy of a case on the hard drive, or on a floppy disc for backup.

8) Printing Case Information:

Go to the "Print Reports" and click:

"Case Detail (All Info)": go to the Print Report menu, choose Print Case Detail (All Info) for all information about the case (Case Information, Medical Chronology, and Significant Information). Prints all documents.

"Medical Chronology by Date": go to the Print Report menu, choose Print Medical Chronology by Date (collects all Medical Chronology Headings and Chronology Entries specific to a Date range, and prints documents).

"Medical Chronology by Doctor": go to the Print Report menu, choose Print Medical Chronology by Doctor (collects all Medical Chronology Headings and Chronology Entries specific to a Doctor, and prints documents).

What is claimed is:

1. A method of generating a medical database for litigation comprising the steps of:

supplying a general medical database having an information section for reviewing medical records and for preparing medical chronology, a drug reference look up section and a drug information section, wherein information in one section of the database may be selectively pasted into another section of the database;

entering specific medical information relative to at least a given litigation in a storage medium, wherein said medical information is entered by selecting a plurality of templates corresponding to specific medical records forms or situations;

displaying, upon entry of the specific medical information a definition or example in the general medical database, wherein at least some terms in the specific medical information are automatically referenced to definitions or examples of such terms in the general medical database such that the selecting of one of the referenced terms in the specific medical information causes the desired information to be displayed.

2. The method of claim 1, wherein the selection of templates further includes the selection of drug information relating to side effects and contraindications.

3. The method of claim 2, wherein the selection of drug information causes the display of the selected drug information.

4. The method of claim 2, wherein the selection of a side effect and contraindication causes the display of the drug particular side effect and contraindication.

5. The method of claim 1, wherein the selection of templates further includes the selection of medical terms, symptoms, diseases and differential diagnosis, medical symbols, abbreviations and acronyms, normal laboratory values, alcohol and drug toxicology, medication indications and wherein the selection of a template causes the corresponding information associated thereto to be displayed.

6. The method of claim 1, wherein the specific medical information includes a medical chronology and upon selecting a term in the medical chronology, a definition or example of the term in the general medical database is displayed.

7. The method of claim 1, wherein actuation of a combined copy-paste command automatically copies and pastes the displayed definition or example or parts thereof to the specific medical information.

8. The method of claim 1, wherein the upon reviewing the specific medical information, selection of a portion of the specific medical information copies the selected portion to a significant information portion, the significant information portion representing parts of the specific medical information that the reviewer thinks are most significant.

9. The method of claim 8 further comprising the step of printing the specific medical information arranged by date, medical provider, or significant information as selected by a user.

* * * * *

UNITED STATES PATENT AND TRADEMARK OFFICE
CERTIFICATE OF CORRECTION

PATENT NO. : 6,128,620

DATED : October 3, 2000

INVENTOR(S) : Patricia L. Pissanos and Stephen M. Beasley

It is certified that error appears in the above-identified patent and that said Letters Patent is hereby corrected as shown below:

On the Title Page, Item [73] Assignee, should read: ---- LeMed, Inc. ----.

Signed and Sealed this

Twenty-ninth Day of May, 2001

*Attest:*

NICHOLAS P. GODICI

*Attesting Officer*  *Acting Director of the United States Patent and Trademark Office*